United States Patent
Bates et al.

(10) Patent No.: US 9,675,526 B2
(45) Date of Patent: Jun. 13, 2017

(54) DEVICE FOR EXTERNAL PERCUTANEOUS CONNECTIONS

(71) Applicant: Cook Medical Technologies LLC, Bloomington, IN (US)

(72) Inventors: Gregory Bates, Advance, NC (US); Hilbert Brown, Winston-Salem, NC (US); Casandra Niebel, Winston-Salem, NC (US); Smitha Raghunathan, Winston-Salem, NC (US); Maximiliano Soetermans, Pinnacle, NC (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 311 days.

(21) Appl. No.: 14/509,585

(22) Filed: Oct. 8, 2014

(65) Prior Publication Data
US 2015/0100039 A1    Apr. 9, 2015

Related U.S. Application Data

(60) Provisional application No. 61/888,220, filed on Oct. 8, 2013.

(51) Int. Cl.
*A61J 15/00* (2006.01)
*A61M 25/01* (2006.01)
(Continued)

(52) U.S. Cl.
CPC ....... *A61J 15/0019* (2013.01); *A61B 1/00089* (2013.01); *A61B 1/018* (2013.01);
(Continued)

(58) Field of Classification Search
CPC .... A61J 15/00; A61J 15/0015; A61J 15/0019; A61J 15/0023; A61J 15/0026;
(Continued)

(56) References Cited

U.S. PATENT DOCUMENTS

| 3,640,281 A | 2/1972 | Robertson |
| 3,920,023 A | 11/1975 | Dye et al. |

(Continued)

FOREIGN PATENT DOCUMENTS

| DE | 39 19 740 A1 | 12/1990 |
| DE | 42 02 844 A1 | 8/1993 |

(Continued)

OTHER PUBLICATIONS

European Patent Office, Rijswijk, Netherlands, International Search Report of International Application No. PCT/US2014/059670, mailed on Jan. 5, 2015, 6 pages.

*Primary Examiner* — Imani Hayman
*Assistant Examiner* — James D Ponton
(74) *Attorney, Agent, or Firm* — Brinks Gilson & Lione

(57) ABSTRACT

The present invention provides devices for creating an external percutaneous fluidic connections. In one embodiment, a needle is configured for extending through an endoscope. The needle includes a distal sharp tip and a lumen extending therethrough. The needle extends out of the endoscope within a body cavity to create an incision through a patient's skin. A safety cap is attached over the distal sharp tip without occluding the needle lumen. A wire is inserted through the needle lumen such that it extends from outside the body at the incision, through the body, and outside the body at the patient's mouth. After removing the needle and the endoscope from the body, a PEG device is coupled to the wire at the patient's mouth, and the PEG device is delivered through the upper GI tract and out through the incision.

20 Claims, 9 Drawing Sheets

(51) Int. Cl.
  *A61M 25/06* (2006.01)
  *A61B 1/00* (2006.01)
  *A61B 17/34* (2006.01)
  *A61B 1/018* (2006.01)
  *A61M 39/02* (2006.01)
  *A61B 90/00* (2016.01)

(52) U.S. Cl.
  CPC ...... *A61B 17/3415* (2013.01); *A61B 17/3494* (2013.01); *A61M 25/0169* (2013.01); *A61M 25/0612* (2013.01); *A61B 17/3478* (2013.01); *A61B 2090/0801* (2016.02); *A61M 2039/0255* (2013.01); *A61M 2210/1053* (2013.01)

(58) Field of Classification Search
  CPC . A61J 15/003; A61J 15/0053–15/0065; A61B 17/3415; A61B 17/3478; A61B 1/00; A61B 1/00064; A61B 1/00071; A61B 1/0008–1/00101; A61M 25/0102; A61M 25/06–25/0693; A61M 39/00–39/0247; A61M 2210/105; A61M 2210/1053
  See application file for complete search history.

(56) References Cited

U.S. PATENT DOCUMENTS

| | | |
|---|---|---|
| 4,573,576 A | 3/1986 | Krol |
| 4,758,219 A | 7/1988 | Sacks et al. |
| 4,834,725 A | 5/1989 | Iwatschenko |
| 5,152,749 A | 10/1992 | Giesy et al. |
| 5,232,443 A | 8/1993 | Leach |
| 5,348,541 A | 9/1994 | Lyell |
| 5,545,141 A | 8/1996 | Eld |
| 5,632,717 A | 5/1997 | Yoon |
| 5,851,195 A | 12/1998 | Gill |
| 2003/0229334 A1 | 12/2003 | Suzuki |
| 2006/0173407 A1 | 8/2006 | Shaughnessy et al. |
| 2007/0016172 A1 | 1/2007 | Charukhchian |
| 2007/0225555 A1 | 9/2007 | Stefanchik |
| 2009/0088599 A1 | 4/2009 | Zook et al. |
| 2010/0094116 A1 | 4/2010 | Silverstein |

FOREIGN PATENT DOCUMENTS

| | | |
|---|---|---|
| EP | 0 127 261 A1 | 12/1984 |
| WO | 96/41576 A1 | 12/1996 |
| WO | 02/19890 A2 | 3/2002 |

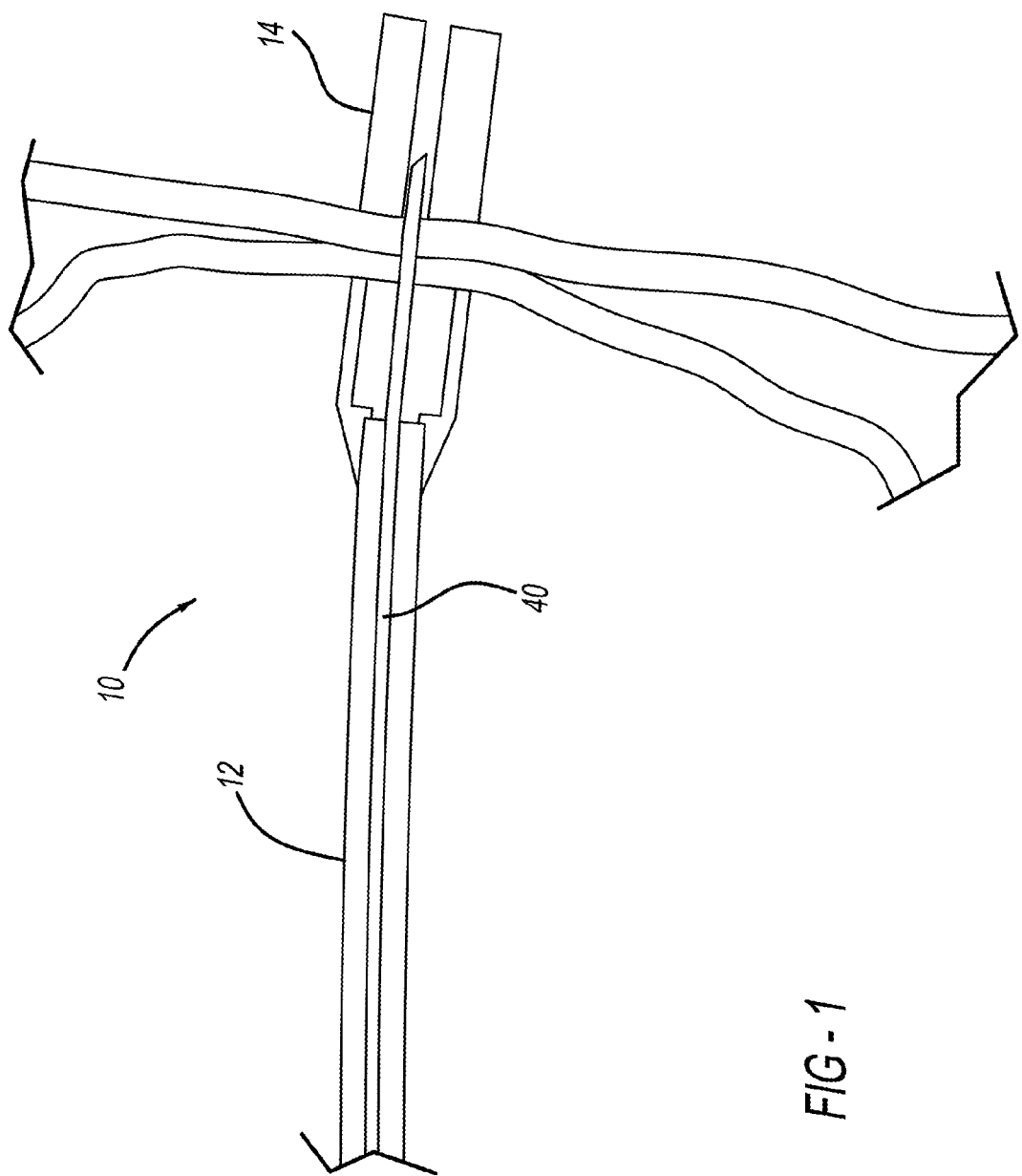

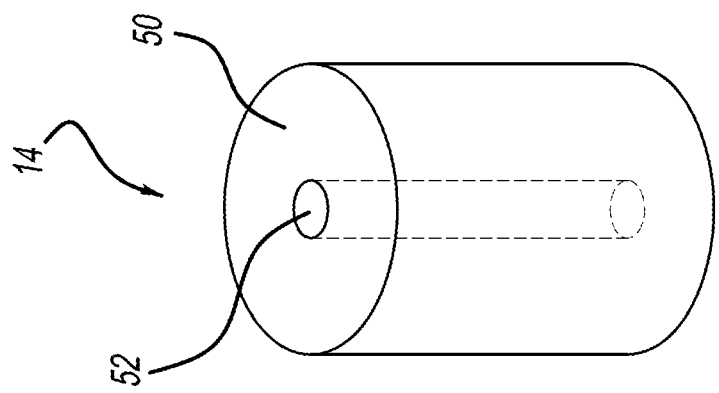
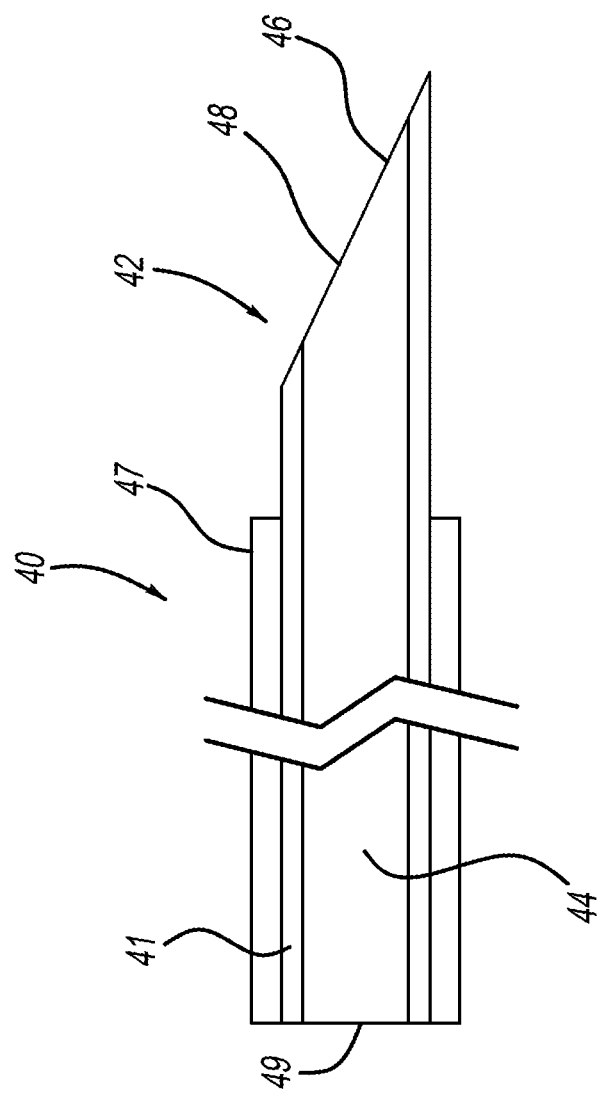

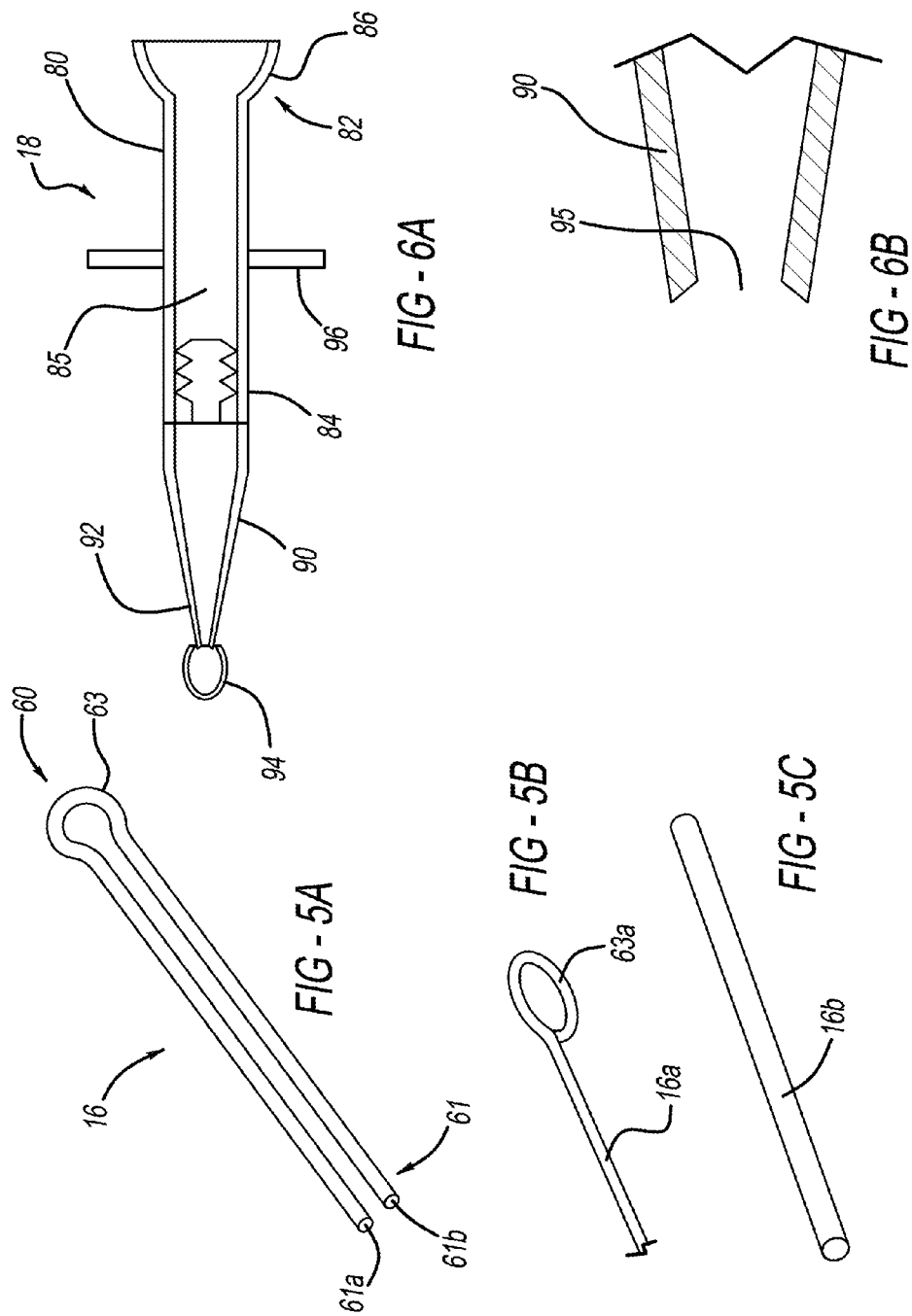

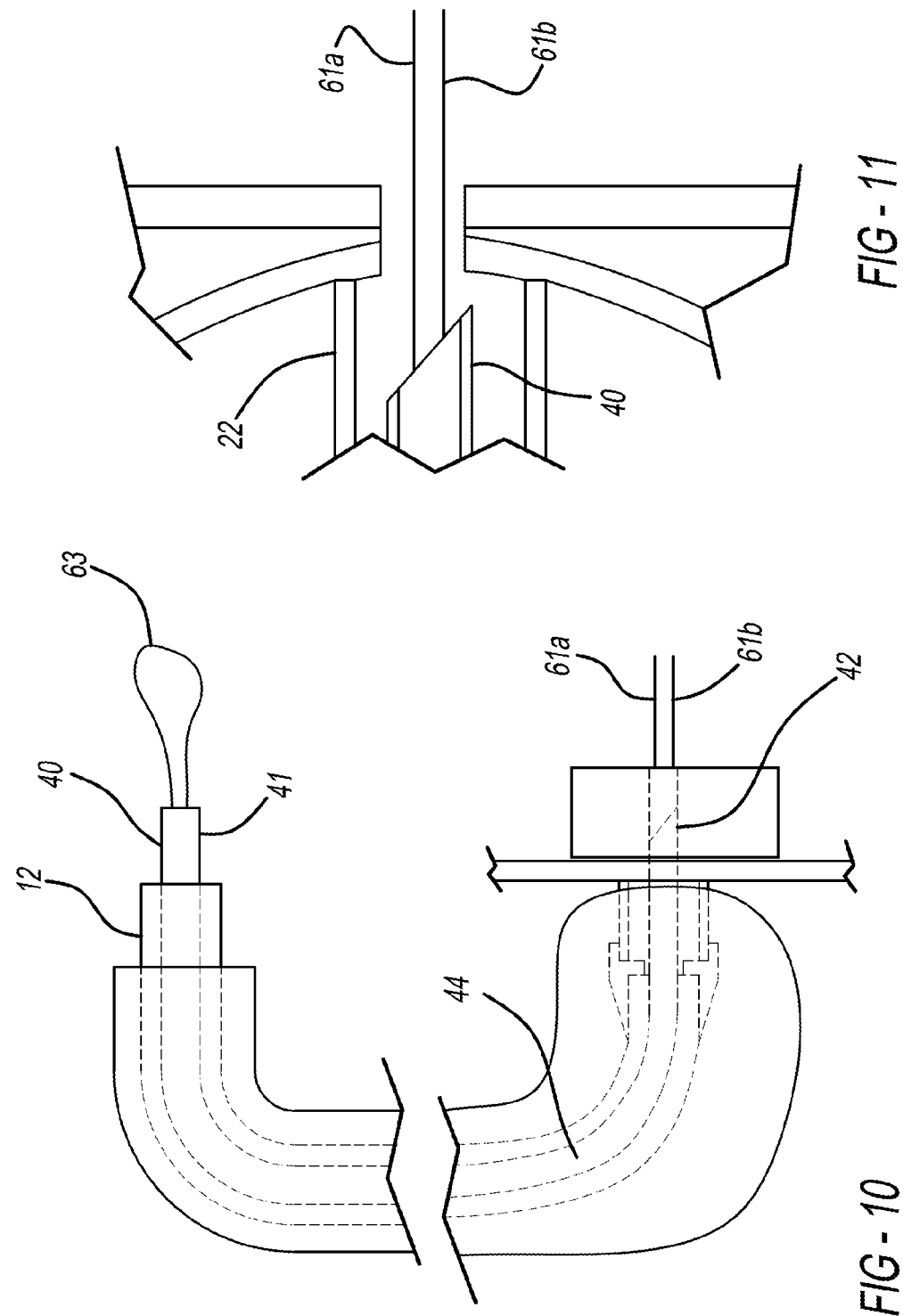

DEVICE FOR EXTERNAL PERCUTANEOUS CONNECTIONS

CROSS-REFERENCE TO RELATED APPLICATIONS

This application claims the benefit of U.S. Provisional Application No. 61/888,220, filed Oct. 8, 2013, which is hereby incorporated by reference in its entirety.

FIELD OF THE INVENTION

The present invention relates generally to external percutaneous connections to an internal organ or bodily lumen.

BACKGROUND OF THE INVENTION

Many types of external percutaneous connections form to provide a patient or medical staff with access to an internal organ or bodily lumen. For example, semi-permanent connections are made through the skin for placement of IV lines, catheters, dialysis lines, colostomy bags in the like. Percutaneous endoscopic gastrostomy tubes, commonly known as PEG tubes, are used as a means of feeding when a person is unable to eat. PEG tubes are typically inserted through a small incision in the abdomen into the stomach. These tubes may be form placed, or large support bolsters having adhesive pad are used to anchor the tube in place such that a portion extends into the stomach, and an opposing portion extends out of the stomach and through the skin for external access.

BRIEF SUMMARY OF THE INVENTION

The present invention provides devices for creating an external percutaneous fluidic connection. In one embodiment, a medical system for facilitating installation of a PEG device into a patient's body by utilizing an endoscope is provided, the system comprising: a needle configured to be disposed within an endoscope lumen of the endoscope and moveable along a longitudinal axis relative to the endoscope, wherein the needle includes a needle lumen extending therethrough; a safety cap for being placed on the outside of the patient's body, the safety cap having a cap lumen extending therethrough, the cap lumen sized and configured to receive and secure the needle such that the needle lumen and cap lumen are in fluid communication; and a wire sized and configured to extend completely through the cap lumen and into the needle lumen.

In another embodiment, a method for creating a percutaneous fluidic connection is provided comprising the steps of: inserting an endoscope into an orifice of a patient, the endoscope having proximal and distal ends and a lumen extending therethrough, wherein the endoscope houses an elongate needle therein having a lumen extending therethrough and a distal sharp tip; advancing the endoscope distally through the patient's upper GI tract and toward a body cavity; advancing the endoscope against an internal surface of a wall of the body cavity; translating the needle housed within the endoscope distally to pierce the internal surface of the body cavity and a skin of the patient with the sharp tip of the needle to define an opening through both the body cavity wall and the outer wall; placing a safety cap over the sharp tip of the needle, wherein the safety cap includes a lumen that receives the needle without occluding the needle lumen; inserting a wire having through the needle lumen, wherein an end of the wire extends out of a distal end of the needle and an opposite end of the wire extends beyond the orifice of the patient; coupling a medical device to the end of folded wire extending beyond the orifice of the patient; and delivering the medical device through the body toward the opening and through the opening.

BRIEF DESCRIPTION OF THE DRAWINGS

FIG. 1 is a schematic view of a system for creating an external percutaneous connection including an endoscope, a needle, and a safety cap;

FIG. 3 is a schematic view of the needle having a needle lumen and an outer sheath;

FIG. 4A is a isometric view of the safety cap having a cap lumen;

FIG. 5A is an isometric view of a wire having a folded configuration and defining a loop;

FIG. 5B is an isometric view of a wire having a straight configuration and defining a loop;

FIG. 5C is an isometric view of a wire having a straight configuration;

FIG. 6A is a schematic view of percutaneous endoscopic gastronomy device;

FIG. 6B is a schematic view of a hole at a distal end of another embodiment of the percutaneous endoscopic gastronomy device;

FIG. 10 is a schematic view showing the wire extending out of both ends of the needle after being inserted through the needle;

FIG. 11 is a schematic view showing the needle retracted into the endoscope after the wire is inserted;

DETAILED DESCRIPTION OF THE INVENTION

Figures 2A, 2B:
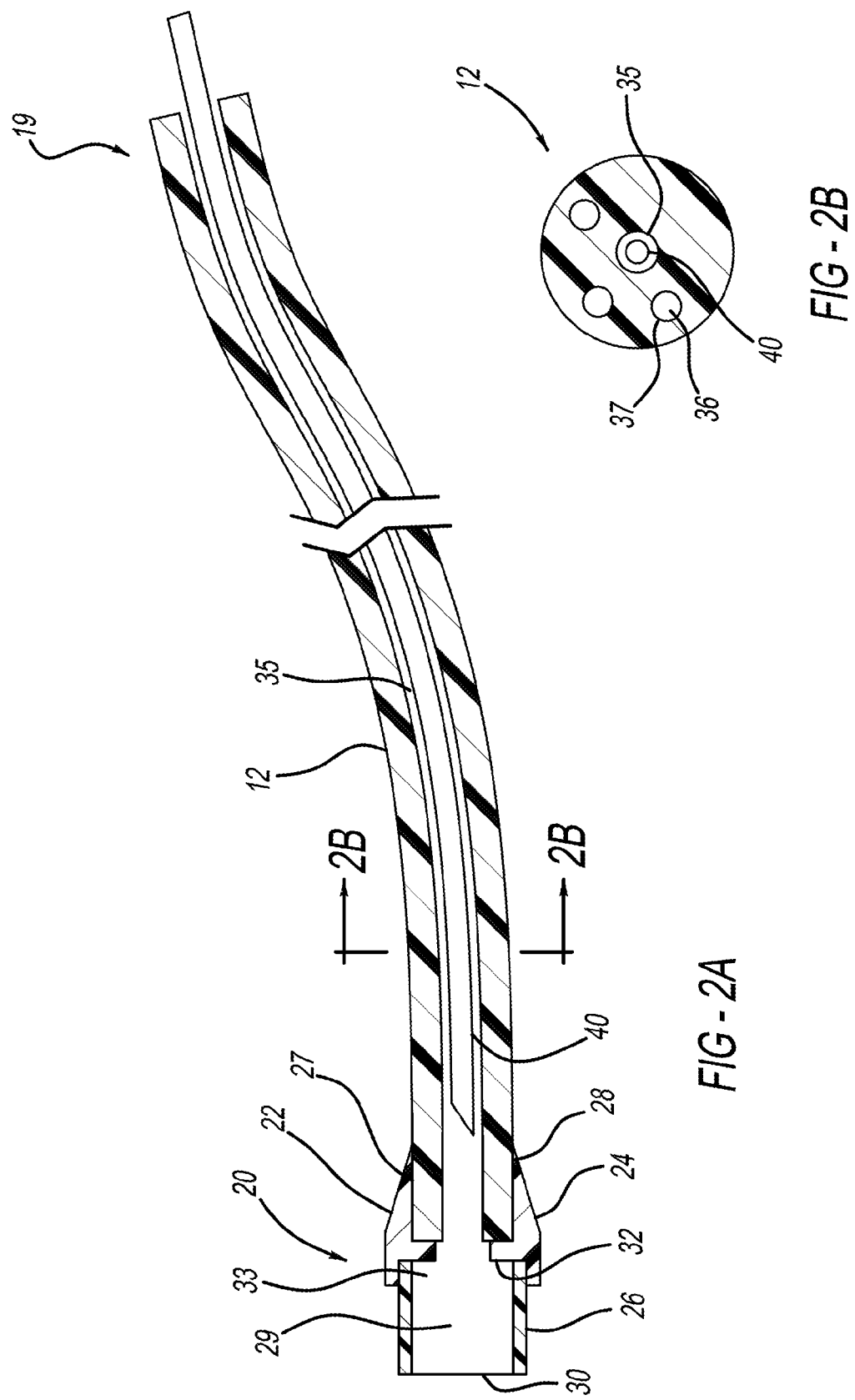
FIG. 2A is a schematic cross-sectional view of the endoscope having the needle disposed therein.
FIG. 2B is a cross-sectional view taken along the line 2B-2B of FIG. 2A showing the needle disposed within a lumen of the endoscope and additional endoscope lumens.

The terms "proximal" and "distal" as used herein are intended to have a reference point relative to the user. Specifically, throughout the specification, the terms "distal" and "distally" shall denote a position, direction, or orientation that is generally away from the user and towards a target site, and the terms "proximal" and "proximally" shall denote a position, direction, or orientation that is generally towards the user and away from a target site. Thus, "proximal" and "distal" directions, portions of a device, or bodily regions, may depend on the point of entry for the procedure (e.g., percutaneously or laparoscopically or endoscopically). References to a friction fit are intended to refer to a tight fit between components where the components are in contact with each other and remain coupled via friction; while the referenced figures may illustrate a gap between the components for ease of illustration, it will be appreciated that the described friction fit is intended.

Turning now to the figures, FIGS. 1-14 illustrate a system 10 including an endoscope 12, an end cap 22, a needle 40, a needle cap 14, a wire 16, and a device 18 for creating an external percutaneous fluidic connection. Generally, the device 18 has been depicted as a gastrostomy feeding device (e.g., a PEG tube), however it will be recognized by those skilled in the art that the device 18 can be applied to form many different external percutaneous connections, including IV lines, internally placed catheters, dialysis lines, colostomy bags and the like. Various known PEG devices can be used as the device 18, which will be described in further detail below.

The endoscope 12 can resemble a typical endoscope or other elongate medical device capable of being inserted into a patient's gastrointestinal tract and toward and into the stomach or other internal bodily organ. One type of endoscopic device capable of use is the Olympus GIF-160, which includes a light, imaging device (e.g. a camera, lens, or the like), water channel, and access channel. The outer diameter of the endoscopic device is approximately 0.59 inches. However, it will be appreciated that various other known endoscopic devices, such as other traditional esophageal diagnostic scopes or "upper" endoscopes, could also be used to fit the desire of the particular user. While the system 10 can be used in various internal organs, reference to the stomach and abdomen will be primarily described.

With reference to FIGS. 2A and 2B, the endoscope 12 has a proximal end 19 and a distal end 20. The proximal end 19 can include a handle (not shown) or other mechanism for manipulating the endoscope 12 through a patient's body and into a desired position within the body. The endoscope 12 is generally flexible while retaining sufficient rigidity to allow it to be pushed through a patient's body toward the target site. The type of endoscope 12 can be a traditional endoscope sized and configured to extend through a patient's mouth, the upper GI tract, and out through a hole in the patient's abdomen. The length of the endoscope 12 can be approximately 160 cm; however, other lengths could also be used that are long enough to extend out of the mouth, through the upper GI tract, and through the patient's abdomen. Thus, it will appreciated that various lengths could apply to patient's having various body sizes.

The distal end 20 of the endoscope 12 can include an end cap 22 with a tapered barrel 24 having a frustoconical shape that tapers from a larger diameter at the distal end and a smaller diameter at the proximal end. The end cap 22 further includes a tube 26 extending distally from the barrel 24. The end cap 22 includes a passageway 27 defining a proximal opening 28, the passageway 27 in communication with a cavity 29 defining a distal opening 30. The cavity 29 is preferably larger than the passageway 27 such that a shelf 32 is defined at the transition between the passageway 27 and the cavity 29. The passageway 27 is sized to receive the endoscope 12 therein, and the end cap 22 can thereby be attached to the endoscope 12 via adhesive, welding, bonding, friction fit, a threaded connection, or the like. The endoscope 12 can contact the shelf 32 such that the shelf 32 acts as a stop to prevent the endoscope 12 from extending into the cavity 29. The passageway 27 is generally sized to correspond to the size of the distal end 20 of the endoscope 12. In a friction fit connection, the passageway 27 is slightly smaller than the outer diameter of the endoscope 12. The barrel 24 is preferably made from a slightly flexible biocompatible polymer to aid in creating a friction fit as well as flex slightly as the endoscope 12 flexes and bends.

The tube 26 is preferably made of a clear plastic or polymer material that is biocompatible, such as a polycarbonate material or other acrylic material. The tube 26 is preferably substantially rigid so that its shape will not deform upon being forced against the inner wall of a patient's stomach by a user. The clear material will allow for a light or imaging device, housed in an accessory channel of the endoscope 12, to have a clear field of view through tube 26 such that the endoscope 12 can perform traditional endoscopic visualization functions. The tube 26 will also protect the end of the endoscope 12 as well as shield the interior of a patient's body from the needle 40 during insertion and retraction of the endoscope 12 and needle 40. The tube 26 will preferably have a wall thickness of about 0.08 inches and a length of about 1 inch. The diameter of the tube 26 can be about 1 inch. Of course, it will be appreciated that these sizes are merely exemplary, and the tube 26, as well as the end cap 22 and barrel 24, can have different sizes to suit the desires of the user or to correspond to the size of the particular endoscope 12 used by the user. The tube 26 can be generally cylindrical in shape, or can taper slightly from a greater proximal outer diameter to a smaller distal diameter.

The barrel 24 can also include a recess 33 at its distal end that is sized to receive the tube 26 therein against the shelf 32. The tube 26 can be attached to the barrel 24 by a friction fit, adhesive, welding, threading, or the like to create the end cap 22. In another form, the end cap 22 can be made as a single unitary piece.

The endoscope 12 further includes at least one longitudinal lumen 35 (e.g. working channel or accessory channel) extending between the proximal and distal ends 19, 20. In one form, the endoscope 12 can include multiple accessory channels and lumens for including various endoscope accessories such as lights or imaging devices or for facilitating medical device delivery, fluids, or the like therethrough. In a preferred form, the endoscope 12 includes a light 36 disposed within a light channel 37 in a manner known in the art.

With reference to FIGS. 2A-3, the endoscope 12 contains the needle 40 that extends through the lumen 35. The needle 40 has proximal and distal ends 41, 42 and a needle lumen 44 extending therebetween. The needle 40 includes a sharp tip 46 at the distal end 42. The sharp tip 46 can be in the form of a bevel or other known needle shape. It will be appreciated that the sharp tip 46 can be any type of tip capable of piercing or puncturing through a patient's stomach and abdomen. The needle lumen 44 extends completely through the needle 40, between a distal opening 48 disposed at the sharp tip 46 and a proximal opening 49 at the proximal end 41. The needle 40 is preferably a 19 gauge needle known for use in the medical field and having a length great than the length of the lumen 35 of the endoscope 12 such that the needle 40 can extend out of both the proximal and distal ends 19, 20 of the endoscope 12 simultaneously. The needle 40 can include a sheath 47 that covers the needle during delivery, from which the needle 40 can extend to pierce through a patient's skin. The needle 40 is configured to typically extend from the sheath 47 up to about 3 inches; however longer needle extensions can also be used to account for piercing thicker body tissue.

The needle 40 can preferably have a length of approximately 180 cm when a 160 cm endoscope is used. Of course, other needle sizes can also be used in accordance with the size of the endoscope used, such that the needle 40 is longer than the endoscope 12 and has a small enough outer diameter that the needle 40 can travel relative to the endoscope 12. For example, a 17 gauge needle could also be used. The preferred gauge of the needle is approximately 19. The inner diameter of the needle 40 is preferably at least 0.024 inches. The outer diameter of the needle 40 is preferably about 0.041 inches. The inner diameter of the sheath generally corresponds to the outer diameter of the needle 40. The outer diameter of the sheath 47 is preferably about 0.066 inches. The lumen 35, through which the needle 40 and sheath 47 extend, is preferably 0.08 inches or greater to allow for needle 40 and sheath 47 to pass through the lumen 35 without undue restriction. The needle 40 is preferably made of stainless steel.

In a delivery configuration, the needle 40 is disposed within endoscope 12 proximally from the end cap 22, as shown in FIG. 2A, such that the sharp tip 46 is protected and shielded during handling of the endoscope 12 and during maneuvering of the endoscope 12 through the patient's body.

The needle 40 is configured to move relative to the endoscope 12 through the endoscope lumen 35. For example, the endoscope 12 can be held stationary, and the needle 40 can be pushed or otherwise advanced distally such that the sharp tip 46 extends beyond the distal end 20 and out of the distal opening 30 of the endoscope 12 and beyond, which will be further described below.

As described above, the system 10 includes the needle cap 14 (e.g. safety cap) shown in FIG. 4A. The needle cap 14 can include a body portion 50 and a longitudinal lumen 52 extending therethrough. The cap 14 can be made of a polymer, rubber, plastic, silicone or other biocompatible material. Preferably, the material used is generally flexible to aid in creating a friction fit with the needle 40 once inserted. In a preferred form, the cap 14 has a generally cylindrical shape; however, a square, rectangular, or other polygonal or other shape can also be used, so long as the outer profile of the cap 14 is larger than the opening in the skin created by the needle 40 after piercing through the abdomen.

The lumen 52 of the cap 14 has a diameter that generally corresponds to an outer diameter of the needle 40. Preferably, the diameter of the lumen 52 is slightly smaller than the outer diameter of the needle 40 so that a friction fit is created when the needle 40 is inserted into the lumen 52 of the cap 14. In one form, the cap 14 has a length of approximately 2 inches to allow a user to grasp and maneuver the cap 14 during insertion of the wire 16 therethrough.

The lumen 52 of the cap 14 is sized such that it can receive and cover the sharp tip 46 of the needle 40 while retaining the needle 40 therein. Thus, the lumen 52 is preferably sized such that the force required to insert the needle 40 into the cap 14 is minimized while still retaining the ability of the cap 14 to prevent the needle 40 from becoming easily removed. The flexible nature of the material of the cap 14 helps retain the needle.

The cap 14, when disposed around the sharp tip 46 of the needle 40, will not occlude the needle lumen 44, such that the area exterior of the cap 14 remains in fluid communication with the needle lumen 44 when the cap 14 is installed. This arrangement maintains access into the needle lumen 44 from outside the cap 14 and access out of the needle lumen 44 toward the outside of the cap 14.

Figure 4C:
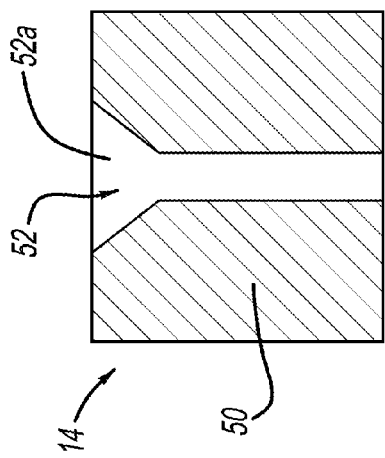
FIG. 4C is a cross-sectional view of another embodiment of the safety cap.
Figure 4D:
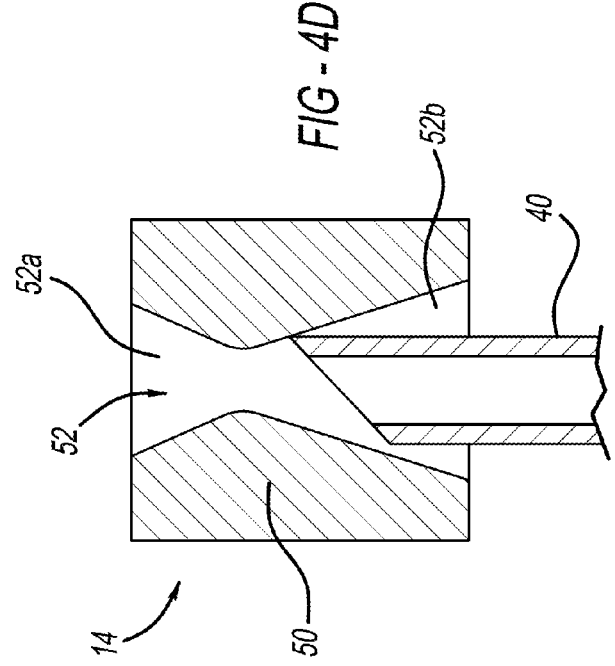
FIG. 4D is a cross-sectional view of another embodiment of the safety cap.
Figure 4B:
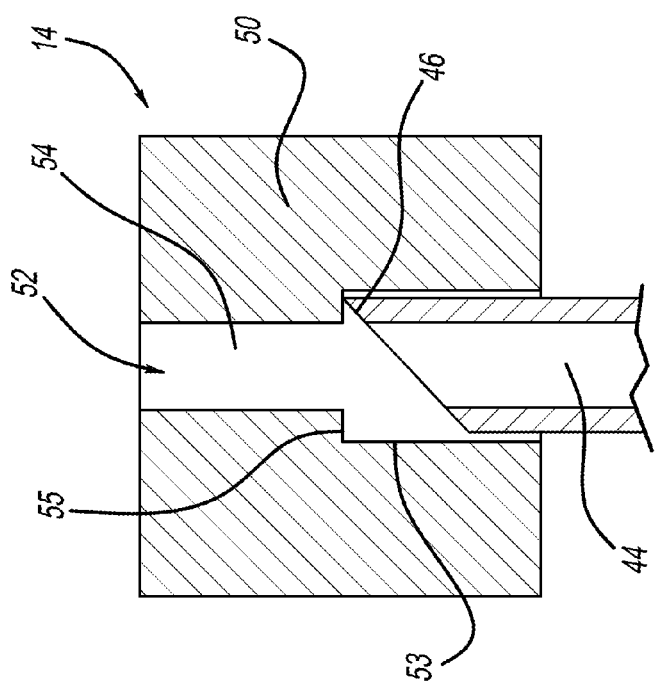
FIG. 4B is a cross-sectional view of another embodiment of the safety cap.

In another approach, shown in FIG. 4B, the lumen 52 of the cap 14 can have two different diameters such that a counter-sunk shape is defined. A diameter of a first portion 53 can be larger than a second portion 54, thereby defining a shelf 55. The first diameter 53 is sized and configured to receive the needle 40, preferably in a friction fit. The diameter 54 of the second portion is sized and configured to generally correspond to the diameter of the needle lumen 44. Thus, the difference in the diameters of the first and second portions 53, 54 is approximately the same as the thickness of the outer wall of the needle 40. In this approach, the shelf 55 will act as a stop, where the tip 46 of the needle 40 contacts the shelf 55 upon insertion into the needle cap 14.

In another approach, the needle lumen 52 can have a different shape. For example, as shown in FIG. 4C, the lumen 52 can have a tapered shape 52a such that the diameter is larger at the outer surface of the body 50 and smaller at a location in the middle of the body 50. This tapered shape can facilitate insertion of the wire 16, further described below, into the lumen 52 and further into the needle lumen 44.

In another form, shown in FIG. 4D, an opposite opening 52b of the lumen 52 can also be tapered in the same manner, such that the needle 40, being inserted into the cap 14, will be easily guided toward the center of the cap 14, while also creating a friction fit when inserted far enough such that the diameter of the lumen 52 is equal or less than the outer diameter of the needle 40.

As described above, the system 10 includes the wire 16. With reference to FIG. 5A-5C, the wire 16 can be made from a typical biocompatible wire material known in the art, but is preferably made stainless steel with Teflon coating. The wire 16 is preferably in the form of braided strands. The wire 16 can be approximately between 150 and 260 cm, such that it is longer than needle lumen 44 so that it can extend out of both ends of the needle 40 simultaneously when inserted. However, the wire 16 could possibly be shorter than the needle 40 but long enough to extend through the patient's body and beyond the patient's mouth, such that after removal of the endoscope 12 and needle 40 the wire 16 extends through the body. The above listed lengths refer to the wire 16 when configured for insertion. As described below, the wire 16 may be folded, so in this configuration the length of the wire 16 would be twice as long as the above described length if the wire 16 were to be unfolded. The wire 16 preferably has a thickness of between 0.010 inch and 0.012 inch so that when folded it can extend through a 0.024 inch needle lumen 44. The wire 16 can have a thickness of about 0.014 inch when used in a straight configuration.

The wire 16 can have a generally folded shape defining proximal and distal ends 60, 61. More specifically, the distal end 61 of the wire includes a pair of wire ends 61a and 61b, and the proximal end 60 defines a loop portion 63 created by the fold in the wire 16.

In another form, a wire 16a is straight and unfolded and includes a closed loop 63a, as shown in FIG. 5B. In this approach, the loop 63a can be closed via crimping or a knot. The knotting can occur before or after the wire is inserted through the needle lumen 44, further described below. In a similar manner, the wire 16a can include the loop 63a at both ends such that a user can insert either end of the wire 16a into the needle lumen 44. Descriptions regarding the use of the wire 16 in a folded condition apply equally to this non-folded embodiment.

In yet another form, as shown in FIG. 5C, a wire 16b can be straight and unfolded and without a loop at the end. In this approach, the wire 16 will be extended through the lumen and subsequently used as a guidewire. The wire 16b is inserted through the needle 40 in the same manner as described with reference to the folded wire 16.

The wire 16 is sized to extend the length of the needle 40 and the endoscope 12 when the wire 16 is folded, so the wire 16, when unfolded, is about twice as long. The wire 16 has a diameter that, when folded, allows the folded wire 16, having the loop portion 63 at the proximal end 60, to fit within the needle lumen 44. The wire 16, when folded, is therefore sized and configured to extend through the needle lumen 44 and between the proximal and distal ends 19, 20 of the endoscope 12 such that a portion of the wire 16 extends out of and is exposed at both the proximal and distal ends 19, 20 of the endoscope 12. However, the wire 16 could still be used even if it doesn't extend out of the needle lumen 44 at the patient's mouth, so as long as it had extended far enough in to the needle lumen 44 to extend out of the mouth when the needle 40 and endoscope 12 are removed. In this case, the wire 16 would extend out of the cap 14 but not out of the needle lumen 44 near the mouth when the needle 40 and endoscope 12 are still extending through the body. Upon removal of the needle 40 and the endoscope 12 from the body, the wire 16 will extend out of the abdomen and the mouth simultaneously.

With reference to FIG. 6A, the device 18 can be a typical PEG device known in the art that are known to be generally pushed through the GI tract toward the stomach or pulled through the GI tract toward the stomach in a manner known in the art. Generally, the device 18 includes an elongate tube 80 that is sized and configured to act as a feeding tube, or the like. The tube 80 has proximal and distal ends 82, 84 and a lumen 85 extending therebetween. The tube 80 can include an anchor portion 86 at the proximal end 82 that extends radially outward from the proximal end of the tube 80 for contacting an inner surface of the stomach to help anchor the device 18 in place. The tube 80 is preferably made of a clear silicone material, but other materials can also be used. The tube 80 is preferably sized about 20 to 24 French, but other sizes could also be used.

The device 18 can further include a dilator portion 90 that envelopes the tube 80. The dilator portion 90 has a tapered or conical shape that tapers to a larger diameter proximally, such that a distal tip 92 of the dilator portion 90 generally forms a point. The dilator portion 90 is generally sized and configured to extend through a percutaneous opening in a patient's skin, thereby dilating the opening so that the remainder of the device 18 can extend through the dilated opening to provide external access into the stomach.

The dilator portion 90 is removably attached to the tube 80, such that after the device 18 has extended through the patient's skin, the dilator portion 90 can be removed, exposing the tube 80.

In another form, the dilator portion 90 and tube 80 are made of a single unitary piece. In this approach, the dilator portion 90 can be cut off to define the end of the tube 80 after the tube 80 has extended through the opening in the patient's abdomen.

The distal tip 92 of the dilator portion 90 can also include an attachment mechanism 94, such as a hook or a closable loop that is sized and configured to be coupled with the loop portion 63 of the wire 16, such that pulling on the wire 16 will in turn pull the device 18 therewith. In another form, the distal tip 92 can include a hole 95 (FIG. 6B) so that the device 18 can be fed over the wire 16 when the wire 16 is not folded and acts as a guidewire.

The tube 80 can further include an attachment mechanism 96 disposed at a location between the anchor portion 86 and the distal end 84 of the tube 80. The attachment mechanism 96 can be any mechanism known in the art for sandwiching the abdominal tissue in the area between the anchor portion 86 and the attachment mechanism 96. For example, the attachment mechanism 96 can be in the form of a removable flange that can slide along the tube 80 and become fixed in position, or it could snap onto the tube 80 in the desired position.

The device 18 has been generally described as a PEG device. It will be appreciated that other known PEG devices capable of being pulled through the GI tract by a wire having a looped end can also be used. Additionally, other tube-like devices for extending through tissue can also be used, including PEG devices and other devices that can be pushed through the upper GI tract over a guidewire.

Thus, the system 10 as described can provide for a safer and faster installation of PEG device or the like while increasing patient comfort. Having described the structure of the system 10, the use of the system 10 and its components will follow, with reference to the figures.

Figure 7:
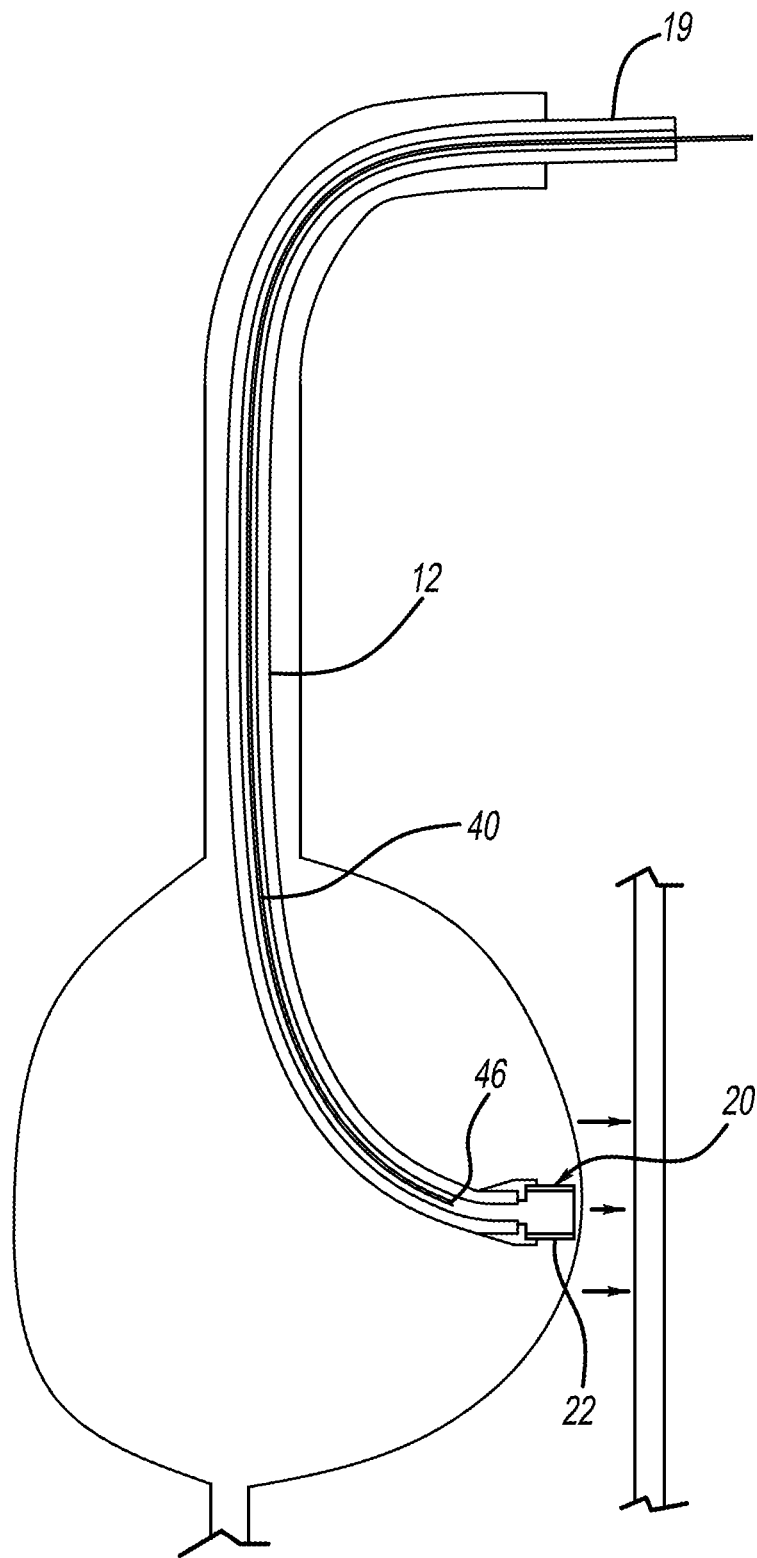
FIG. 7 is a schematic view showing the endoscope inserted through an upper GI tract of a patient into the patient's stomach.

With reference to FIG. 7, the endoscope 12 is introduced into the patient's body via a bodily orifice such as, preferably, a natural orifice. Natural orifices can include, for example, the mouth or the nose, but it will be appreciated that other natural bodily orifices can also be used to insert the endoscope 12. In another form, the endoscope can be inserted through a non-naturally occurring orifice, such as through a percutaneous incision. Preferably, the endoscope 12 is inserted through the mouth in a manner known in the art.

The endoscope 12 includes the needle 40 disposed within the lumen 35, such that the sharp tip 46 is disposed proximally from the distal end 20 of the endoscope 12. Therefore, as the endoscope 12 is inserted through the patient, the sharp tip 46 and the needle 40 will be shielded to limit trauma caused by unintentional contact between the needle 40 and the patient's internal anatomy. The needle 40, being housed within the endoscope 12, is therefore translated along with the endoscope 12 in a delivery configuration.

The endoscope 12 is guided through the patient's upper GI tract toward the stomach or other internal bodily organ where installation of the device 18 is desired. In the case of a PEG device such as a feeding tube, the stomach is the preferable ultimate location.

Once the distal end 20 of the endoscope 12 has reached the stomach, the location of the endoscope 12 within the stomach can be monitored using an imaging device of the endoscope 12 in a manner known in the art. Alternatively, or in addition to the use of an imaging device, the endoscope 12 can illuminate a light from the distal end 20, which can be seen from outside the patient's body due to illumination of the skin.

As shown in FIG. 7, the distal end 20 of the endoscope 12, including the end cap 22 attached thereto, is pressed against an internal surface of the stomach to force the stomach wall toward the abdominal wall. This will cause the space between the stomach and the abdominal wall to become reduced or eliminated at the location of the distal end 20 of the endoscope 12. Other bodily organs or fluid in the area between the stomach and the abdominal wall will generally be caused to move away from the distal end 20 of the endoscope 12.

Figure 8:
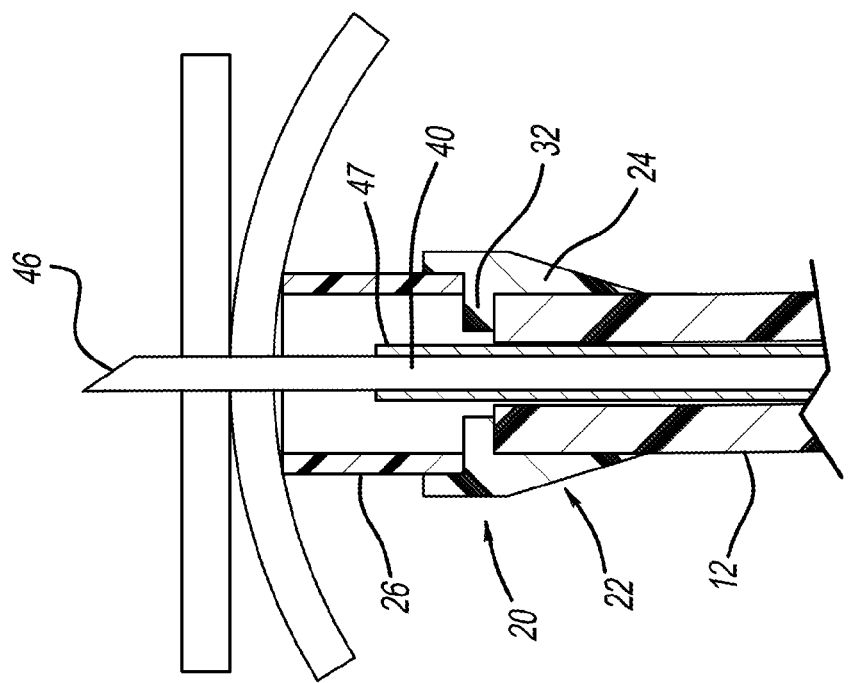
FIG. 8 is a schematic view showing the needle extending out of the endoscope and through the patient's skin to create an incision.
Figure 13:
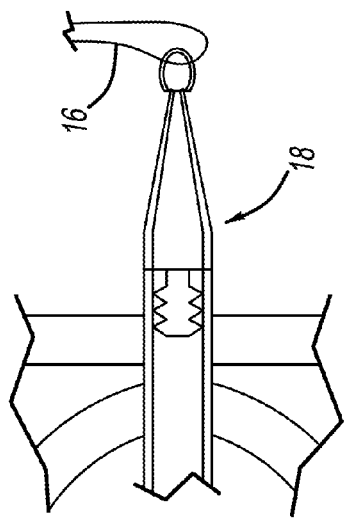
FIG. 13 is a schematic view showing a dilator portion extending through the incision and the wire removed from the body.

With reference to FIG. 8, with the stomach and abdominal wall being pressed against each other due to the pressure exerted by the endoscope 12, the needle 40 can be advanced distally toward the stomach and abdominal wall by user manipulation at the proximal end 19 of the endoscope. The sharp tip 46 of the needle 40 will extend through the end cap 22 and tube 26 that was previously shielding the needle 40. More specifically, the needle 40 and sheath 47 will be translated distally out of the endoscope 12 but still within the tube 26. The needle 40 will then extend out of the sheath 47 and toward the inner surface of the stomach, where it will pierce of puncture through the stomach and the abdominal wall. The sheath 47 and end cap 22 remain within the patient's body. This configuration of the needle is known as the deployed configuration.

This method of piercing the stomach and abdomen from within the stomach via the needle 40 and endoscope 12 is faster and more reliable than prior methods. In prior methods, for example, a trocar would be used to pierce the abdomen from the outside such that the trocar would enter the stomach. However, this method would require a manner of locating the desired position on the abdomen that would lead to the desired entry into the stomach. By piercing from within the stomach, the incision is reliably made such that the stomach is easily accessed.

After piercing the stomach and abdominal wall, the sharp tip 46 of the needle 40 will extend fully through the abdominal wall such that the sharp tip 46 and a portion of the needle 40 are exposed outside of the patient's body.

Figure 9:
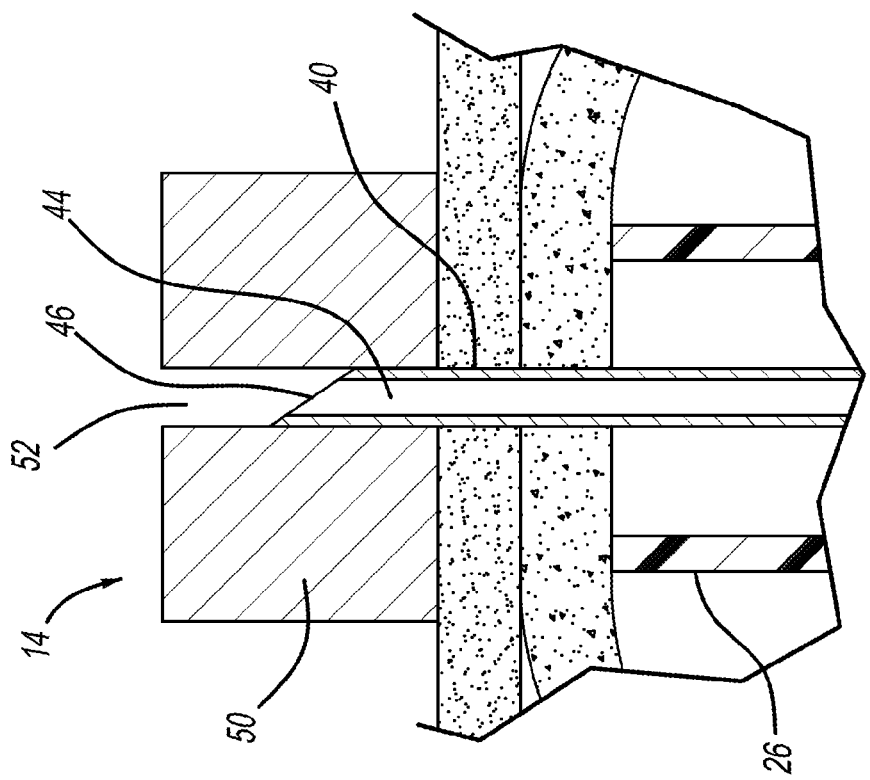
FIG. 9 is a schematic view showing the needle covered by the safety cap.

With reference to FIG. 9, the needle cap 14 is subsequently placed over the sharp tip 46 of the needle 40. More specifically, the lumen 52 receives the sharp tip 46 and a portion of the needle 40. The needle cap 14 will preferably retain the needle 40 by a friction fit between the lumen 52 and the needle 40. In another form, the body portion 50 of the cap 14 can be compressed or clamped to cause the lumen 52 to engage and grab the needle 40 to increase or create the friction fit. The needle 40 preferably extends about 1 inch into the cap 14, but could extend greater or less than that distance, as long as the needle 40 is retained by a friction fit. Preferably, the needle 40 is inserted at least about ½ inch to provide a sufficient friction fit.

The body portion 50 of the cap 14, being larger and wider than the incision created by the needle 40, will prevent the needle 40 from being pulled back into or migrating back into the stomach, while providing a robust and safe connection for the user to grasp during insertion of the wire 16.

As described above, the needle 40 includes a needle lumen 44. The cap 14, after receiving the needle 40 in the cap lumen 52, does not occlude the needle lumen 44, so the needle lumen 44 is open to the exterior of the patient's body.

The proximal end 41 of the needle 40 will extend out of the patient's mouth or other orifice through which the endoscope 12 was initially inserted. The distal end 42 of the needle 40, including the sharp tip 46, is retained by the cap 14. The needle lumen 44 is therefore open at both the proximal and distal ends 41, 42 of the needle 40.

With reference to FIG. 10, the wire 16, being folded to define the loop portion 63, is subsequently inserted into the needle lumen 44 and pushed such that it extends completely through the needle lumen 44. The wire 16 can be inserted from either end of the needle lumen 44, so long as the loop portion 63 extends out of the proximal end 41 of the needle 40 (near the patient's mouth). Thus, the wire ends 61a, 61b can be inserted into the needle 40 at the proximal end 41 and pushed toward the distal end 42, where they exit the needle lumen 44 at the needle cap 14. Or, the loop portion 63 can be inserted at the distal end 42 of the needle 40 and pushed toward the proximal end 41. In either case, the wire ends 61a, 61b will extend out of the needle 40 at the cap 14, and the loop portion 63 will extend out of the needle 40 at the patient's mouth. However, in the event the wire 16 is not long enough to extend out of both ends of the needle 40, the wire 16 may still be extended enough such that it is past the patient's mouth and will be exposed upon retraction of the endoscope 12 and needle 40 from the patient's body. In this case, the wire 16 extends out of the cap 14 but not out of the needle 40 when the needle and endoscope 12 are disposed within the body. Upon removal of the needle 40 and endoscope 12, the wire 16 will extend out of both the abdomen and the mouth.

With reference to FIG. 11, with the wire 16 extending between the abdominal incision and the patient's mouth, the cap 14 can be removed from the needle 40 and set aside. The needle 40 will then be free to travel longitudinally along the wire 16 and back into the patient's body. The needle 40 can then be retracted back into the end cap 22 and into the endoscope 12 such that the needle 40 is disposed proximally of the distal end 20 of the endoscope 12. The needle 40 and endoscope 12 can then be retracted from the patient's body, leaving the wire 16 in place.

Figure 12:
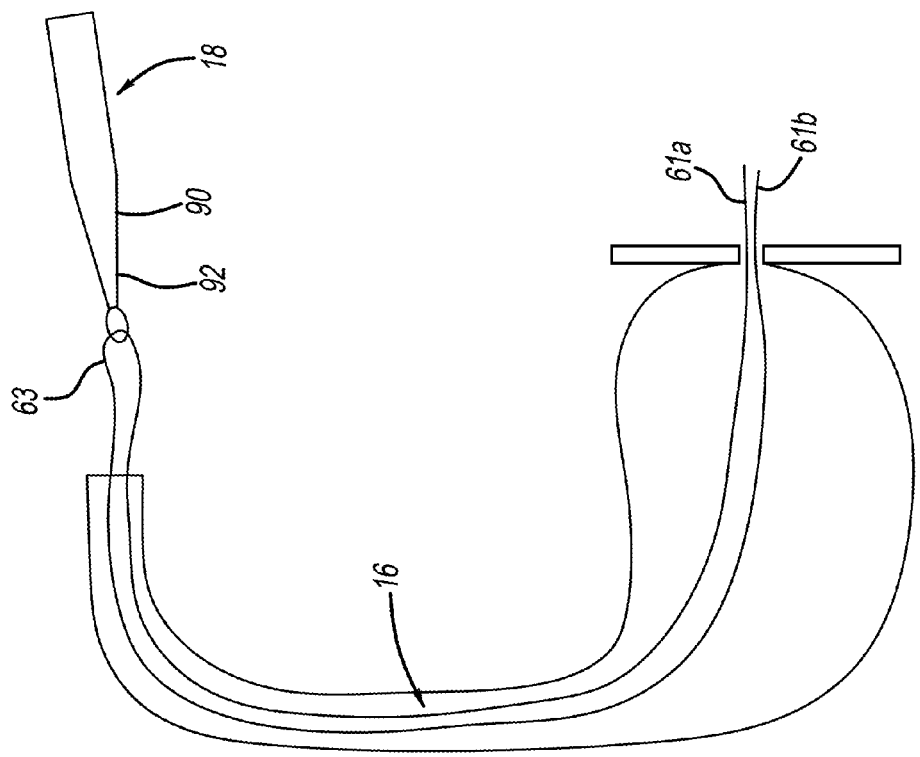
FIG. 12 is a schematic view showing the gastronomy device attached to the wire with the endoscope and needle removed from the body.

With reference to FIG. 12, the wire 16 is in place and extending out of the patient's mouth with the wire ends 61a, 61b extending out of the incision in the abdomen. The device 18 can be attached to the loop portion 63 adjacent the patient's mouth. More specifically, the distal tip 92 of the dilator 90 is attached to the loop portion 63 of the wire 16. The device 18 is therefore in position to be pulled through the patient's upper GI tract in a manner known in the art.

This approach is faster and more reliable than prior pull methods, where a snaring device was inserted through the upper GI tract toward the stomach. The snaring device would grab a looped end of a wire and the snaring device and wire would be pulled through the upper GI tract toward and out of patient's mouth. This required coupling the snaring device to the wire inside the stomach, adding a level of complexity relative to the method disclosed herein.

With the wire 16 extending through the body, the wire ends 61a, 61b can be grasped at the location of the abdominal incision and pulled, thereby pulling the device 18 through the upper GI tract. When the dilator 90 reaches the location of the incision within the stomach, the dilator 90 will increase the size of the opening of the incision in a manner known in the art as the dilator 90 extends through the stomach and abdominal walls. With the dilator 90 extending through the opening, the wire 16 has thus been removed fully from the patient's body.

Figure 14:
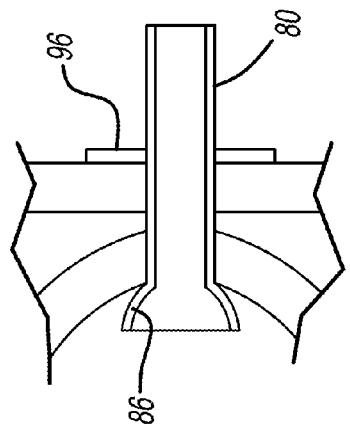
FIG. 14 is a schematic view showing the gastronomy device extending through the patient's skin.

With reference to FIG. 14, the dilator 90 can be removed in a manner known in the art leaving the tube 80 extending through the abdominal opening. The device 18 can then be anchored in a manner known in the art such that the tube is fixed. With the device 18 in place, it can be connected to a food supply or the like.

The foregoing approach described the use of a folded wire 16 and a pull method where the device 18 is pulled through the upper GI tract by the wire, such that the wire 16 is removed from the body as the dilator portion 90 is correspondingly pulled through the incision in the abdomen. A similar approach can be used for a straight wire having a loop at the end instead of the described folded wire.

In an alternative approach, a straight wire 16 having no loop at the end can be inserted through the needle 40 in the same manner. However, rather than attaching the distal tip 92 of the dilator 90 to a looped end of the wire 16, the dilator 90 and tube 80 can be inserted over the wire 16, which can act as a guidewire. In this approach, a typical pusher member or tube (not shown) as known in the art can be used to push the device 18 along the wire 16 from the mouth through the esophagus toward the abdomen. In this approach, the wire 16 is not pulled, and will remain extending through the dilator 90 and tube 80 after the dilator 90 has extended through the abdomen. Once the device 18 is extending through the patient's skin, the wire 16 can be retracted either at the abdomen or at the patient's mouth leaving the tube in place as shown in FIG. 14.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical system for facilitating installation of a PEG device in a patient's body by utilizing an endoscope, the system comprising:
   a needle configured to be disposed within an endoscope lumen of the endoscope and moveable along a longitudinal axis relative to the endoscope, wherein the needle includes a needle lumen extending therethrough;
   a safety cap for being placed on the outside of the patient's body, the safety cap having a cap lumen extending longitudinally therethrough, the cap lumen sized and configured to receive and secure the needle such that the needle lumen and cap lumen are in fluid communication, the cap lumen sized and structured to frictionally engage the needle to secure the needle to the safety cap; and
   a wire sized and configured to extend completely through the cap lumen and through at least a portion of the needle lumen.

2. The system of claim 1, further comprising an end cap configured for attachment to a distal end of the endoscope.

3. The system of claim 2, wherein the end cap includes a generally cylindrical tube extending distally from a tapered barrel, the barrel having a passageway sized to the receive the endoscope.

4. The system of claim 3, wherein the end cap defines a shelf extending transversely within the passageway.

5. The system of claim 1, wherein the wire is folded to define a looped end and a pair of wire ends, and the wire is sized and configured to extend completely through the needle lumen when folded.

6. The system of claim 5, wherein the looped end of the wire extends proximally from a proximal end of the needle in a deployed configuration and the pair of wire ends extend distally from the distal end of the needle in the deployed configuration.

7. The system of claim 1, wherein the wire has a delivery configuration and a deployed configuration, the wire extends out of one of the needle lumen and the cap lumen in the delivery configuration, and the wire extends out of both the needle lumen and the cap lumen in the deployed configuration.

8. The system of claim 1, wherein the safety cap has an attached configuration and a distal end of the needle is disposed within the safety cap lumen.

9. The system of claim 1, wherein the safety cap lumen has a first diameter and a second diameter, the first diameter is greater than the second diameter, and the safety cap lumen defines a shelf.

10. The system of claim 1, wherein the safety cap lumen includes at least one tapered portion for facilitating insertion of the wire or needle therein.

11. The system of claim 1, wherein the needle lumen is in fluid communication with an exterior of the safety cap through the safety cap lumen such that the needle lumen is not occluded by the safety cap when the needle is received within the safety cap.

12. The system of claim 1 further comprising a PEG device having an attachment mechanism at a distal end thereof, wherein the attachment mechanism is configured to couple with the wire such that the PEG device can be pulled by the wire.

13. A medical system for facilitating installation of a PEG device in a patient's body by utilizing an endoscope, the system comprising:
   a needle configured to be disposed within an endoscope lumen of the endoscope and moveable along a longitudinal axis relative to the endoscope, wherein the needle includes a needle lumen extending therethrough;
   a safety cap for being placed on the outside of the patient's body, the safety cap having a cap lumen extending longitudinally therethrough, the cap lumen sized and configured to receive and secure the needle such that the needle lumen and cap lumen are in fluid communication, wherein the cap lumen has a first diameter and a second diameter, the first diameter being greater than the second diameter to define a shelf; and
   a wire sized and configured to extend completely through the cap lumen and through at least a portion of the needle lumen;
   wherein a distal end of the needle contacts the shelf when the needle is inserted into the safety cap lumen.

14. The system of claim 13, wherein the safety cap lumen has a diameter that is smaller than an outer diameter of the needle to create a friction fit when the needle is inserted into the safety cap lumen.

15. A method for creating a percutaneous fluidic connection, the method comprising:
   inserting an endoscope into an orifice of a patient, the endoscope having proximal and distal ends and a lumen extending therethrough, wherein the endoscope houses an elongate needle therein having a lumen extending therethrough and a distal sharp tip;
   advancing the endoscope distally through the patient's upper GI tract and toward a body cavity;
   advancing the endoscope against an internal surface of a wall of the body cavity;
   translating the needle housed within the endoscope distally to pierce the internal surface of the body cavity and a skin of the patient with the sharp tip of the needle to define an opening through both the body cavity wall and the skin;
   placing a safety cap over the sharp tip of the needle, wherein the safety cap includes a lumen that is sized and structured to frictionally engage the needle without occluding the needle lumen;

inserting a wire through the needle lumen, wherein an end of the wire extends out of a distal end of the needle and an opposite end of the wire extends beyond the orifice of the patient;

coupling a medical device to the end of the wire extending beyond the orifice of the patient;

delivering the medical device through the body toward the opening and through the opening.

16. The method of claim 15, wherein the wire is folded to define a loop and the medical device is coupled to the loop and pulled through the body.

17. The method of claim 15, wherein the wire is a straight wire and the medical device includes an opening, the wire is inserted through the medical device, and the medical device is pushed along the wire through the body.

18. The method of claim 15 further comprising removing the endoscope and the needle from the body prior to coupling the medical device to the wire.

19. The method of claim 18, wherein the needle is removed prior to the endoscope.

20. The method of claim 15, wherein the wire is pushed through the entire needle lumen without the use of a snaring device within the patient's body.

* * * * *